(12) United States Patent
Bora et al.

(10) Patent No.: US 9,588,058 B1
(45) Date of Patent: Mar. 7, 2017

(54) NON-DESTRUCTIVE EVALUATION OF WATER INGRESS IN PHOTOVOLTAIC MODULES

(71) Applicant: Lawrence Livermore National Security, LLC, Livermore, CA (US)

(72) Inventors: Mihail Bora, Livermore, CA (US); Jack Kotovsky, Alameda, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 14/983,076

(22) Filed: Dec. 29, 2015

(51) Int. Cl.
*G01N 21/94* (2006.01)
*G01N 21/95* (2006.01)
*G01N 21/88* (2006.01)
*H02S 50/15* (2014.01)
*G01N 21/958* (2006.01)

(52) U.S. Cl.
CPC ......... *G01N 21/94* (2013.01); *G01N 21/8851* (2013.01); *G01N 21/958* (2013.01); *H02S 50/15* (2014.12); *G01N 2021/8887* (2013.01)

(58) Field of Classification Search
CPC ....... G01N 2021/8887; G01N 21/8851; G01N 21/94; G01N 21/958; H02S 50/15
See application file for complete search history.

(56) References Cited

PUBLICATIONS

Kurtz et al., "Photovoltaic Module Qualification Plus Testing," National Renewable Energy Laboratory, Dec. 2013, pp. 1-29.
Bora et al., "Multiplexed gas spectroscopy using tunable VCSELs," SPIE Defense, Security, and Sensing, International Society for Optics and Photonics, Mar. 2012, 6 pages.
Kempe, M., "Modeling of rates of moisture ingress into photovoltaic modules," Solar Energy Materials & Solar Cells, vol. 90, No. 16, Oct. 2006, pp. 2720-2738.
Kapur et al., "Determination of moisture ingress through various encapsulants in glass/glass laminates," Photovoltaic Specialists Conference (PVSC), 2009 34th IEEE, Jun. 2009, pp. 1210-1214.
Trigg, A., "Applications of Infrared Microscopy to IC and MEMS Packaging," IEEE Transactions on Electronics Packaging Manufacturing, vol. 26, No. 3, Jul. 2003, pp. 232-238.
Kempe et al., "Evaluation of moisture ingress from the perimeter of photovoltaic modules," Progress in Photovoltaics: Research and Applications, vol. 22, Issue 11, Nov. 2014, pp. 1159-1171.
Iwamoto et al., "Interaction of Water in Polymers: Poly(ethylene-co-vinyl acetate) and Poly(vinyl acetate)," Journal of Polymer Science: Part B: Polymer Physics, vol. 43, Feb. 10, 2005, pp. 777-785.
Iwamoto et al., "Interactions of Water with OH Groups in Poly(ethylene-co-vinyl alcohol)," Journal of Polymer Science: Part B: Polymer Physics, vol. 44, Issue 17, Sep. 1, 2006, pp. 2425-2437.

*Primary Examiner* — Mark R Gaworecki
(74) *Attorney, Agent, or Firm* — Zilka-Kotab, PC

(57) ABSTRACT

Systems and techniques for non-destructive evaluation of water ingress in photovoltaic modules include and/or are configured to illuminate a photovoltaic module comprising a photovoltaic cell and an encapsulant with at least one beam of light having a wavelength in a range from about 1400 nm to about 2700 nm; capture one or more images of the illuminated photovoltaic module, each image relating to a water content of the photovoltaic module; and determine a water content of the photovoltaic module based on the one or more images. Systems preferably include one or more of a light source, a moving mirror, a focusing lens, a beam splitter, a stationary mirror, an objective lens and an imaging module.

20 Claims, 3 Drawing Sheets

NON-DESTRUCTIVE EVALUATION OF WATER INGRESS IN PHOTOVOLTAIC MODULES

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to water ingress in photovoltaic devices, and more particularly, this invention relates to non-invasive investigation of water ingress into photovoltaic devices using hyperspectral infrared imaging.

BACKGROUND

The ingress of water into photovoltaic modules is known to cause performance loss related to corrosion, mechanical stress and optical transmittance degradation of encapsulating polymer. It is estimated that 2% of photovoltaic modules fail within 8 years of operation and that 16% of these failures are related to encapsulant degradation. Due to the long lifetime of modules (30 years) this problem is difficult to avoid even by using low water diffusivity materials. Mitigation approaches include the use of moisture barriers (glass) for the front and back sheet of the module as well as sealing the edges with desiccant filled polymers.

To evaluate durability and resistance to water ingress, conventional techniques involve incubating the photovoltaic module in hot, damp conditions for an extended period, such as 85 centigrade and 85% humidity for a period of 1000 hours.

After incubation, measurement of water content can be accomplished using one of two conventional techniques. First, measurement may be accomplished destructively by taking samples from different sections of the module. Second, measurement may be accomplished by using colorimetric reporters such as calcium films that exhibit a change in optical properties upon interaction with water.

Destructive evaluation has the downside that it is time consuming and measurement on the same module cannot be repeated, limiting the amount of collected data. Colorimetric tests, while non-destructive, can undesirably alter diffusion kinetics, may present additional issues related to integration with the fabrication processing, and cannot be performed on existing deployed modules unless those modules already contain appropriate reporter compounds.

There is therefore a need for fast, large-scale and stand-off evaluation method of water ingress that can reliably predict failure in photovoltaic modules.

SUMMARY

In one embodiment, a system for non-destructive evaluation of water ingress in photovoltaic modules includes: a light source; a moving mirror positioned in a beam path of the light source; a focusing lens positioned in the beam path of the light source and between the light source and the moving mirror; a beam splitter positioned in the beam path of the light source between the light source and the moving mirror; a stationary mirror positioned adjacent the beam splitter and outside the beam path of the light source; a photovoltaic module positioned opposite the stationary mirror and outside the beam path of the light source; an objective lens positioned between the beam splitter and the photovoltaic module, the objective lens being outside the beam path of the light source; and an imaging module configured to capture two-dimensional spectral image data relating to a water content of the photovoltaic module.

In another embodiment, a method for non-destructive evaluation of water ingress in photovoltaic modules includes illuminating a photovoltaic module comprising a photovoltaic cell and an encapsulant with at least one beam of light having a wavelength in a range from about 1400 nm to about 2700 nm; capturing one or more images of the illuminated photovoltaic module, each image relating to a water content of the photovoltaic module; and determining a water content of the photovoltaic module based on the one or more images.

Other aspects and advantages of the present invention will become apparent from the following detailed description, which, when taken in conjunction with the drawings, illustrate by way of example the principles of the invention.

BRIEF DESCRIPTION OF THE DRAWINGS

For a fuller understanding of the nature and advantages of the present invention, as well as the preferred mode of use, reference should be made to the following detailed description read in conjunction with the accompanying drawings.

DETAILED DESCRIPTION

Figure 1:
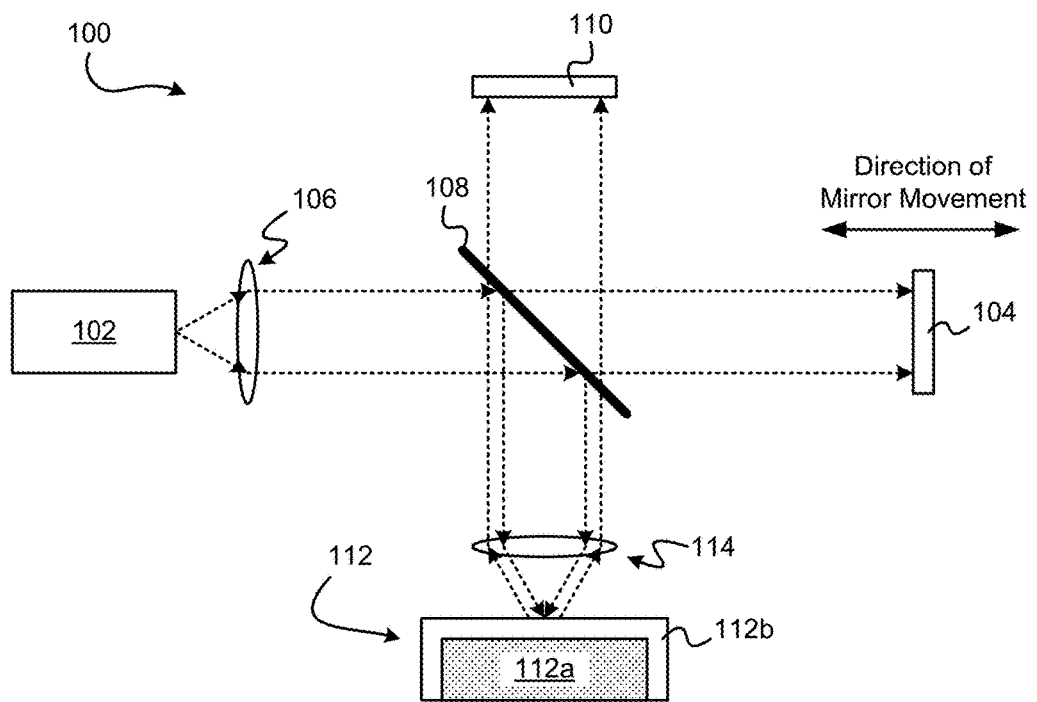
FIG. 1 is a simplified schematic drawing of a non-destructive water ingress investigation system, according to one embodiment of the presently disclosed inventive concepts.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of non-destructive evaluation of water ingress into photovoltaic modules, and/or related systems and methods.

In one embodiment, a system for non-destructive evaluation of water ingress in photovoltaic modules includes: a light source; a moving mirror positioned in a beam path of the light source; a focusing lens positioned in the beam path of the light source and between the light source and the moving mirror; a beam splitter positioned in the beam path of the light source between the light source and the moving mirror; a stationary mirror positioned adjacent the beam splitter and outside the beam path of the light source; a photovoltaic module positioned opposite the stationary mirror and outside the beam path of the light source; an objective lens positioned between the beam splitter and the photovoltaic module, the objective lens being outside the beam path of the light source; and an imaging module configured to capture two-dimensional spectral image data relating to a water content of the photovoltaic module.

In another embodiment, a method for non-destructive evaluation of water ingress in photovoltaic modules includes illuminating a photovoltaic module comprising a photovoltaic cell and an encapsulant with at least one beam of light having a wavelength in a range from about 1400 nm to about 2700 nm; capturing one or more images of the illuminated photovoltaic module, each image relating to a water content of the photovoltaic module; and determining a water content of the photovoltaic module based on the one or more images.

The presently disclosed inventive concepts are directed to a non-invasive optical detection system and techniques based on hyperspectral near infrared imaging of photovoltaic modules. Briefly, the photovoltaic modules are illuminated with a narrow wavelength beam covering at least one water absorption band, e.g. at 1400 nm, 1900 nm, and/or 2700 nm, and investigated for the presence of water. If the spectral range revealed under illumination overlaps one or more, preferably several, absorption lines of water, it is possible to achieve high resolution moisture evaluation corresponding to differential image acquisition on and/or off absorption lines.

Experimental evidence demonstrates estimation of differential absorbance suggests a change in intensity of approximately 3% between on and off absorbance imaging for 0.1% moisture content. Notably, since most of the materials used in fabrication of photovoltaic modules such as glass, silicon, polymers, or aluminum are either transparent or reflective, photovoltaic modules typically do not exhibit large changes in extinction for the spectral region considered, advantageously providing limited interference with the differential absorbance of water.

However, a key challenge is presented by adapting the technique to modules with complex structure made of multiple layers with various material properties, composition and roughness. Because the surfaces are not optically perfect, resolution issues related to scattering off grain boundaries and interfaces arise. To an extent, this problem is mitigated by the relatively large expected diffusion length of moisture (on the order of centimeters).

Another potential issue is related to water-polymer interaction influence on the infrared absorption spectrum as hydrogen bonding of water to functional groups alter molecular absorbance spectrum both as a red spectral shift and as line width broadening as a result of hydrogen bonding of water to polymeric chemical functional groups.

Accordingly, these descriptions propose an approach to determine water ingress across an entire photovoltaic cell, even in non-transparent samples. Two routes for multispectral imaging may be employed, in various embodiments.

For the first, the image(s) will be acquired in transmission reflection (transflection) mode at the photovoltaic cell surface with light passing through and being absorbed by the encapsulant. This enables high-definition investigation of the photovoltaic cell surface and water ingress through the encapsulant to this surface.

For the second, the image(s) will be acquired at the glass encapsulant surface to exploit Kramers-Kronig changes in refractive index near absorption bands. Image processing algorithms for background subtraction, calibration with respect to infrared peaks of encapsulant material, and removal of artifacts not related to chemical content may be employed to improve the investigation process.

Turning now to the figures, FIG. 1 depicts a system 100 for non-destructive evaluation of water ingress into photovoltaic modules using hyperspectral infrared imaging, in accordance with one embodiment. As an option, the present system 100 may be implemented in conjunction with features from any other embodiment listed herein, such as those described with reference to the other FIGS. Of course, however, such system 100 and others presented herein may be used in various applications and/or in permutations which may or may not be specifically described in the illustrative embodiments listed herein. Further, the system 100 presented herein may be used in any desired environment.

As shown in the embodiment represented by FIG. 1, the system 100 includes a light source 102; a moving mirror 104 positioned in a beam path of the light source; a focusing lens 106 positioned in the beam path of the light source and between the light source and the moving mirror; a beam splitter 108 positioned in the beam path of the light source between the light source and the moving mirror; a stationary mirror 110 positioned adjacent the beam splitter and outside the beam path of the light source; a photovoltaic module 112 positioned opposite the stationary mirror and outside the beam path of the light source; an objective lens 114 positioned between the beam splitter and the photovoltaic module, the objective lens being outside the beam path of the light source; and an imaging module (not shown) configured to capture two dimensional spectral image data relating to a water content of the photovoltaic module 112.

In one embodiment, the light source may comprise a fiber and may also include the imaging component, e.g. as a probe. Using a fiber light source allows application of the presently disclosed inventive techniques to devices that are typically not subject to optical investigation because the device cannot be placed in a sample cell or compartment. Accordingly, the system 100 is configured for use with macro scale devices and to investigate water ingress in contexts not possible using conventional systems.

Preferably, the photovoltaic module 112 includes a photovoltaic portion 112a and an encapsulant 112b configured to prevent or retard water ingress to the photovoltaic portion 112a.

Of course, the system 100 may include additional and/or alternative components, features, etc. as described herein and as would be understood by a person having ordinary skill in the art upon reading these descriptions, without departing from the scope of the present disclosure. Preferably, additional and/or alternative components or features include one or more of the following.

In one approach, the imaging module is configured to capture the two-dimensional spectral image data using transmission reflection. In another embodiment, the imaging module is configured to capture the two-dimensional spectral image data at an interface between a photovoltaic cell of the photovoltaic module and an encapsulant of the photovoltaic module.

In another approach, the imaging module is configured to capture the two-dimensional spectral image data at an interface between an encapsulant of the photovoltaic module and air surrounding the photovoltaic module.

In some approaches, as mentioned above, the photovoltaic module is non-transparent.

The encapsulant may be disposed on a substrate comprising a material selected from a group consisting of glass, silicon, a polymer and a metal, in various approaches. More particularly, the polymer may include one or more of ethylene vinyl acetate and a polyvinyl butryal resin matrix, and/or the metal may include aluminum.

In more embodiments, the light source is tunable to produce beam(s) of light having a wavelength in a range from about 1400 nm to about 2700 nm. In particularly preferred approaches, the light source is tunable to at least about 1400 nm, about 1900 nm, and about 2700 nm wavelengths, as these wavelengths correspond to known absorption lines in the absorptions spectrum of water. Of course, other wavelengths, e.g. for known absorption lines of encapsulant material after interaction with water (such as water/polymer hydrogen bonding interactions) may also be advantageous to employ, in various embodiments.

The two dimensional spectral image data, in various embodiments, may include a series of monochromatic images representing an infrared absorption spectral fingerprint of water content across at least one surface of the photovoltaic module. For example, the surface(s) may include an the air/encapsulant interface, a surface within the encapsulant, a surface at the encapsulant/photovoltaic cell interface, etc. as would be understood by a person having ordinary skill in the art upon reading the present descriptions.

Figure 2:
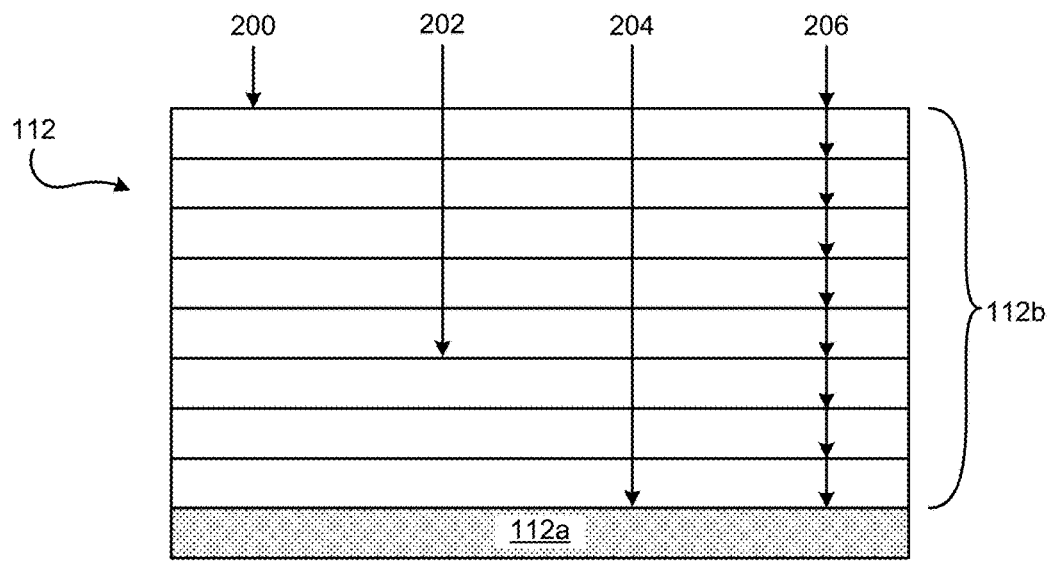
FIG. 2 is a simplified schematic of a photovoltaic module shown from a side view, according to one embodiment of the presently disclosed inventive concepts.

Now with reference to FIG. 2, a simplified schematic of a photovoltaic module 112 is shown from a side view, according to one embodiment. As discussed above with reference to system 100, the photovoltaic module 112 generally includes a photovoltaic material 112a, and one or more encapsulant layers 112b each being formed from one or more encapsulant materials such as glass, polymers, etc. as would be understood by a person having ordinary skill in the art. Preferably, the photovoltaic module includes a photovoltaic cell 112a and a plurality of encapsulant layers 112b. The photovoltaic cell or material 112a may optionally be disposed on a substrate (not shown), and the encapsulant layer(s) 112b may encapsulate the photovoltaic cell 112a and/or substrate on as few as one to as many as all sides thereof.

With continuing reference to FIG. 2, in various approaches of the presently disclosed inventive concepts investigating water ingress into photovoltaic devices such as photovoltaic module 112 includes illuminating the photovoltaic module with one or more beams of light, e.g., beams 200, 202, 204 and 206. As will be appreciated by a skilled artisan upon reading these descriptions, the beam(s) of light may be configured to investigate water ingress at multiple locations within the photovoltaic module, and/or to perform hyperspectral investigation of water ingress at a single location or multiple locations within the photovoltaic module, in various approaches.

By "configured" what is meant is that properties of the beam allow the light to penetrate certain materials of the photovoltaic module, e.g. encapsulant material, and allow the light to be absorbed by other materials of interest, e.g. encapsulant material, photovoltaic material, or any other material disclosed herein, to allow investigation of water ingress thereto. Exemplary properties which may be modified to configure beams of light include wavelength, frequency, amplitude, etc. as would be understood by a skilled artisan upon reading the present disclosure.

For instance, in one approach a beam of light 200 may be configured to investigate water ingress at an interface between the photovoltaic module and the surrounding environment, i.e., at the photovoltaic module outer surface.

In another approach a beam of light 202 may be configured to penetrate one or more layers 112b of encapsulant material and investigate water ingress to a predetermined depth within the encapsulant of the photovoltaic module 112.

In yet another approach a beam of light 204 may be configured to penetrate all layers 112b of the encapsulant and investigate water ingress at the photovoltaic material/cell 112a.

Figure 3A:
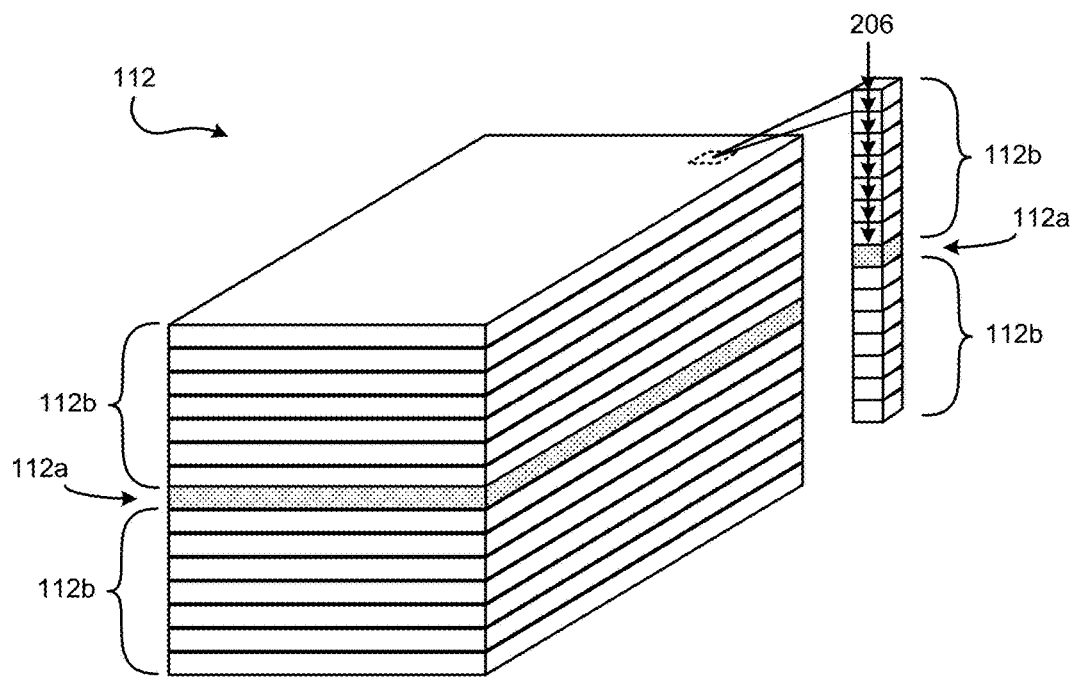
FIG. 3A is a simplified schematic of a photovoltaic module shown from a three-dimensional view, according to one embodiment of the presently disclosed inventive concepts.

In still yet another approach, a beam or beams of light 206 may be configured to investigate water ingress at one or more, perhaps each, layer 112b of encapsulant and/or the photovoltaic material/cell 112a. The beam(s) 206 may successively illuminate the photovoltaic module 112 and investigate water ingress in a stepwise fashion, as shown in FIG. 3A and as would be understood by a skilled artisan reading the present descriptions, according to one embodiment.

Figure 3B:
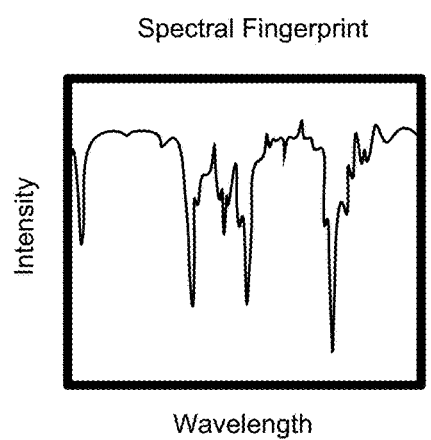
FIG. 3B is a simplified schematic of a spectral fingerprint, according to one embodiment of the presently disclosed inventive concepts.
Figure 3C:
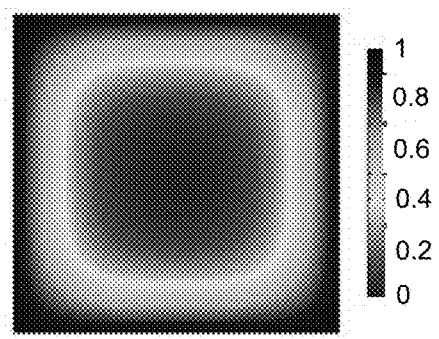
FIG. 3C depicts a representative two-dimensional mapping of water ingress across a photovoltaic module surface, according to one embodiment of the presently disclosed inventive concepts.

In more approaches, multiple beams 200, 202, 204, and/or 206 may be employed to provide a two and/or three dimensional mapping of water ingress across a particular layer, surface, cross section, or volume of the photovoltaic module. For example, according to one embodiment FIG. 3C depicts a result obtained from two-dimensional mapping of water ingress for a photovoltaic module comprising an ethylene vinyl acetate (EVA) photovoltaic cell having a thickness of 0.5 mm encapsulated by double glass laminate exhibiting saturation values of 0.0055 concentration at surface, and diffusion coefficient $10^{-6}$ $cm^2/s$. The exemplary mapping corresponds to a portion of the photovoltaic module having an area of approximately 156×156 mm. The exemplary result shown in FIG. 3C may be generated based on observing the spectral fingerprint of the photovoltaic module across a plurality of locations within the 156×156 mm area, and determining water presence and/or concentration at each location, then assembling the result into a two dimensional map.

Preferably, hyperspectral imaging is employed, such that multiple beams having different wavelengths are used to investigate a particular location in the photovoltaic module, and more preferably each particular location of interest in the photovoltaic module.

For instance, in one practical embodiment each pixel of an imaging device may be mapped to a location on the photovoltaic module, and each mapped location on the photovoltaic module may be subjected to hyperspectral imaging while illuminating the mapped location with multiple beams of light having different wavelengths.

Most preferably, the multiple beams of light have wavelength(s) that correspond to one or more known infrared absorption lines for water, as well as wavelength(s) that do not correspond to a known infrared absorption line for water. For example, preferred embodiments utilize multiple beams of light corresponding to a known infrared absorption line for water, at least some of which employ a wavelength of about 1400 nm, other of which employ a wavelength of about 1900 nm, and/or still other of which employ a wavelength of about 2700 nm.

In more embodiments, multiple beams of light which do not correspond to a known infrared absorption line for water are employed, having one or more wavelengths having a range between 1400 nm and 1900 nm, or between 1900 nm and 2700 nm. Of course, other embodiments may employ other wavelengths for the beams which do not have a wavelength corresponding to a known infrared absorption line for water without departing from the scope of the present disclosures.

Preferably, at least one beam having a wavelength corresponding to a known infrared absorption line for water, and at least one beam having a wavelength not corresponding to a known infrared absorption line for water, are employed for each location of interest within the photovoltaic module, allowing for differential analysis of hyperspectral images and comparison of spectral fingerprint (see e.g. FIG. 3B) both on- and off the water infrared absorption lines.

For instance, in one approach a photovoltaic module or other component includes an encapsulant comprising a layered structure such as shown in FIG. 2 or 3A, etc. Each layer of the encapsulant may include a material having a different composition, e.g. a plurality of different polymers such as ethylene vinyl acetate, polyvinyl butryal resin, etc. as would be understood by a person having ordinary skill in the art upon reading the present descriptions.

Preferably, each layer in the structure has a known position, such that the layered structure is also an ordered structure with a series of different materials arranged in layers (e.g. 112b as shown in FIGS. 2 and 3A) expanding outward, e.g. concentrically, from a photovoltaic portion (e.g. 112a as shown in FIGS. 2 and 3A). The ordered layering advantageously permits rapid, non-invasive and non-destructive evaluation of depth of water ingress, in preferred approaches.

In particular, in one embodiment it is advantageous to analyze each layer to obtain the spectral signature for each of the different materials in each layer, and identify particular regions for the particular material that indicate presence of water in that layer (e.g. in a region substantially in the vicinity of one or more of 1400 nm, 1900 nm, and/or 2700 nm bands as set forth above).

Subsequently, the module may be subjected to a multi-layer analysis to obtain the IR spectrum thereof, and one or more of the particular spectral regions identified in the above process may be investigated to determine whether a particular one or more of the materials/layers of the encapsulant have been exposed to/include water. In this manner, it is advantageously possible to investigate the existence of water in a particular layer of interest (rather than simply the module, encapsulant, or photovoltaic portion, as a whole). Using a priori knowledge regarding the ordering of the layers, it is also possible to determine a precise depth of water ingress into the layered structure. These techniques therefore offer an improvement to the precision and specificity with which water ingress may be investigated in a particular module.

In addition, according to more embodiments photovoltaic modules may include a moisture barrier layer, comprising a material configured to prevent diffusion of water and thus barring ingress of water from the environment to the interior portions of the photovoltaic module when the moisture barrier layer is arranged to surround those interior portions. However, for various reasons (e.g. chemical degradation, physical damage, etc.) the moisture barrier may experience a failure, and permit water ingress, risking damage or failure to the photovoltaic module.

It would be advantageous to be able to determine whether a moisture barrier layer has experienced such a failure prior to damage occurring to the photovoltaic portion of the photovoltaic module, as the photovoltaic portion may be removed and/or the encapsulant replaced/repaired before the photovoltaic portion is irreversibly damaged.

Accordingly, in one embodiment of the presently disclosed inventive concepts, a photovoltaic module may be investigated as described herein, but may be subjected to a desiccation procedure prior to hyperspectral imaging in order to evaporate any water present in layers of the encapsulant between the moisture barrier layer and an external environment.

As will be understood by skilled artisans upon reading the present descriptions, if a moisture barrier layer has experienced a failure, then water may be permitted to penetrate the moisture barrier layer and ingress to the interior portion of the module. However, the desiccation process does not effectively evaporate water present in the interior portion of the module, at least in part due to the fact that functional portions of the moisture barrier layer prevent or discourage diffusion of water back across the barrier into the external portions of the module.

In particularly preferred approaches, the desiccation procedure is configured such that water present in the portion of the module interior to the moisture barrier layer is not evaporated, e.g. by selectively heating the module or an external portion thereof without similarly heating the interior portions, and/or heating the module for a predetermined amount of time at a predetermined temperature calculated to cause evaporation in external portions of the module without causing similar evaporation/diffusion of water within the internal portions.

In any event, water remaining in the internal portions of the module after the desiccation process indicates failure of the moisture barrier layer, since a functioning moisture barrier layer would not permit water to penetrate the barrier and enter the interior portions. Accordingly detecting presence of water interior to a moisture barrier layer of a photovoltaic module represents a valuable failure detection technique that still enables the photovoltaic portion of the module to be recovered prior to experiencing water damage.

Accordingly, the presently disclosed inventive concepts include, in one embodiment, desiccating a module as described above, and investigating one or more materials interior to a moisture barrier layer to evaluate the presence or absence of water. Presence or absence of water may be determined using any suitable technique described herein, such as investigating a layer of interest known to be positioned interior to the moisture barrier layer for a spectral signature, e.g. in a region in the vicinity of 1400 nm, 1900 nm, and/or 2700 nm, indicative of presence of water therein.

Figure 4:
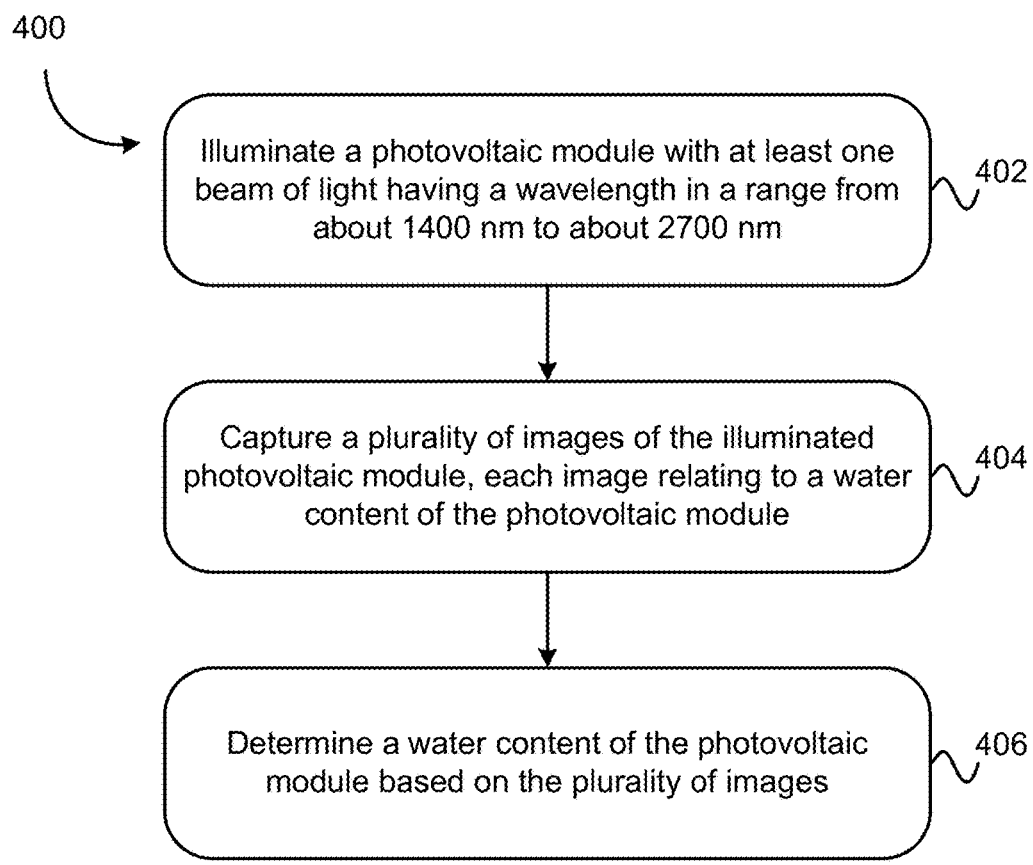
FIG. 4 is a flowchart of a method, according to one embodiment of the presently disclosed inventive concepts.

FIG. 4 shows a method 400 for non-destructive evaluation of water ingress in photovoltaic modules, in accordance with one embodiment. As an option, the present method 400 may be implemented for non-destructive evaluation of water ingress in photovoltaic modules such as those shown in the other FIGS. described herein. Of course, however, this method 400 and others presented herein may be used for non-destructive evaluation of water ingress in photovoltaic modules which may or may not be related to the illustrative embodiments listed herein. Further, the methods presented herein may be carried out in any desired environment. Moreover, more or less operations than those shown in FIG. 4 may be included in method 400, according to various embodiments. It should also be noted that any of the aforementioned features may be used in any of the embodiments described in accordance with the various methods.

As shown in FIG. 4, method 400 includes operation 402, in which a photovoltaic module comprising a photovoltaic cell and an encapsulant is illuminated with at least one beam of light having a wavelength in a range from about 1400 nm to about 2700 nm. Illuminating the photovoltaic module with the beam(s) of light allows the non-destructive investigation of water ingress without requiring presence of a colorimetric substance in the photovoltaic module.

Method 400 also includes operation 404, where a plurality of images of the illuminated photovoltaic module are captured. Notably, each image relates to a water content of the photovoltaic module.

With continuing reference to FIG. 4, method 400 further includes operation 406, which involves determining a water content of the photovoltaic module based on the plurality of images. The determination may be based on one or more image processing algorithms configured specifically for processing hyperspectral infrared image data, e.g. monochromatic images, and include background subtraction, calibration with respect to various encapsulant material(s), identification of artifacts not relating to chemical content, etc. as would be understood by a person having ordinary skill in the art upon reading the present descriptions.

Of course, in additional and/or alternative approaches, method 400 may include one or more additional and/or alternative features, operations, etc. as would be understood by a skilled artisan reading the present descriptions.

For instance, in some embodiments of method 400 capturing the plurality of images includes performing differential image acquisition on and off one or more absorption lines of water. In other words, a single location may be imaged when illuminated using a beam of light having a wavelength corresponding to a known absorption line of water, and subsequently (or previously) imaged when illuminated using a beam of light having a wavelength not corresponding to a known absorption line of water. The absorption spectra resulting from each illumination may be imaged and compared to investigate the presence and/or amount of water in the photovoltaic module. Preferably, the plurality of images are monochromatic images.

In more approaches, the method 400 includes illuminating the photovoltaic module with a plurality of beams of light. Each beam of light may have a different wavelength in the range from about 1400 nm to about 2700 nm. Preferably, the method also includes capturing one of the plurality of images when illuminating the photovoltaic module with each of the plurality of beams of light. In this manner, a series of images captured when illuminating the photovoltaic module using beams of light having different wavelengths are captured, facilitating differential analysis and investigation of water ingress.

In some approaches, accordingly, each of the plurality of images relate to the water content of a single location on the photovoltaic module.

In some approaches, the photovoltaic module is nontransparent. In these embodiments, it is particularly advantageous to utilize transmission reflection to investigate water ingress into the photovoltaic module. Thus, the illuminating and the capturing may include transmission reflection, and the plurality of images preferably depict a surface of the photovoltaic cell. In such embodiments, the image(s) acquired in transmission reflection (transflection) mode at the photovoltaic cell surface investigate light passing through and being absorbed by the encapsulant. This enables high-definition investigation of the photovoltaic cell surface and water ingress through the encapsulant to this surface.

In other embodiments, e.g. those leveraging Kramers-Kronig changes in refractive index near absorption bands, the plurality of images depict a surface of the encapsulant and are used to investigate water ingress through this surface.

The method may also include mapping chemical composition of the photovoltaic module across two dimensions based on the plurality of images, in various embodiments.

The hyperspectral imaging method may also be adapted to microscopy measurements for further insight in moisture ingress kinetics at micro-scale for a better mechanistic understanding on how water accumulates in polymer pores. Moisture diffusion through encapsulants may be carried out in a custom setup for ethylene vinyl acetate films deposited on various substrates (glass, silicon, metal) in conjunction with supplemental stressors, such as: ultra violet illumination, applied potential, current density, mechanical stress, temperature. Addition of stressors allows investigation into the presence of synergistic effects from exposure to multiple stressors and identify effects on the diffusion coefficient and water vapor transfer rate (WVTR) as well as temporal evolution of water ingress in photovoltaic modules.

Advantageously, implementation of the presently disclosed inventive concepts may provide a field-deployed rapid screening tool that can measure moisture ingress in hundreds of modules per day under a variety of weathering conditions, identifying items that are more prone to damage and thus allowing for mitigation measures before failure occurs.

Similarly, implementation of these inventive concepts enables investigation of individual materials, layers, or sets of one or more materials and/or layers to precisely determine whether water ingress has occurred at a particular location (e.g. depth, position) in a module, and/or whether a particular material (e.g. a layer of interest) has been exposed to water.

Further still, by desiccating modules prior to investigation, it is possible to specifically investigate whether a moisture barrier of a particular module has failed, before the module itself fails to perform in a photovoltaic capacity, permitting repair after the moisture barrier has failed but before the valuable photovoltaic portion is damaged by water.

The inventive concepts disclosed herein have been presented by way of example to illustrate the myriad features thereof in a plurality of illustrative scenarios, embodiments, and/or implementations. It should be appreciated that the concepts generally disclosed are to be considered as modular, and may be implemented in any combination, permutation, or synthesis thereof. In addition, any modification, alteration, or equivalent of the presently disclosed features, functions, and concepts that would be appreciated by a person having ordinary skill in the art upon reading the instant descriptions should also be considered within the scope of this disclosure.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:
1. A system for non-destructive evaluation of water ingress in photovoltaic modules, comprising:
   a light source;
   a moving mirror positioned in a beam path of the light source;

a focusing lens positioned in the beam path of the light source and between the light source and the moving mirror;

a beam splitter positioned in the beam path of the light source between the light source and the moving mirror;

a stationary mirror positioned adjacent the beam splitter and outside the beam path of the light source;

an objective lens positioned between the beam splitter and the photovoltaic module, the objective lens being outside the beam path of the light source; and an imaging module configured to capture two-dimensional spectral image data relating to a water content of a photovoltaic module positioned opposite the stationary mirror and outside the beam path of the light source.

2. The system as recited in claim 1, wherein the imaging module is configured to capture the two-dimensional spectral image data using transmission reflection.

3. The system as recited in claim 1, wherein the imaging module is configured to capture the two-dimensional spectral image data at an interface between a photovoltaic cell of the photovoltaic module and an encapsulant of the photovoltaic module.

4. The system as recited in claim 1, wherein the imaging module is configured to capture the two-dimensional spectral image data at an interface between an encapsulant of the photovoltaic module and air surrounding the photovoltaic module.

5. The system as recited in claim 1, wherein the photovoltaic module is non-transparent.

6. The system as recited in claim 1, wherein the photovoltaic module comprises a photovoltaic cell and an encapsulant.

7. The system as recited in claim 6, wherein the encapsulant is disposed on a substrate comprising a material selected from a group consisting of glass, silicon, a polymer and a metal.

8. The system as recited in claim 7, wherein the polymer comprises one or more of ethylene vinyl acetate and a polyvinyl butryal resin matrix, and wherein the metal comprises aluminum.

9. The system as recited in claim 1, wherein the light source is tunable to produce light having a wavelength in a range from about 1400 nm to about 2700 nm.

10. The system as recited in claim 1, wherein the two dimensional spectral image data comprise a series of monochromatic images representing an infrared absorption spectral fingerprint of water content across at least one surface of the photovoltaic module.

11. A method for non-destructive evaluation of water ingress in photovoltaic modules, comprising:

illuminating a photovoltaic module comprising a photovoltaic cell and an encapsulant with at least one beam of light having a wavelength in a range from about 1400 nm to about 2700 nm;

capturing one or more images of the illuminated photovoltaic module, each image relating to a water content of the photovoltaic module; and determining a water content of the photovoltaic module based on the one or more images.

12. The method as recited in claim 11, wherein capturing the one or more images comprises performing differential image acquisition on and off one or more absorption lines of water.

13. The method as recited in claim 11, wherein the one or more images are monochromatic images.

14. The method as recited in claim 11, comprising illuminating the photovoltaic module with a plurality of beams of light, each beam of light having a different wavelength in the range from about 1400 nm to about 2700 nm.

15. The method as recited in claim 14, comprising capturing one of the one or more images when illuminating the photovoltaic module with each of the plurality of beams of light.

16. The method as recited in claim 15, wherein each of the one or more images relate to the water content of a single location on the photovoltaic module.

17. The method as recited in claim 11, wherein the illuminating and the capturing comprise transmission reflection, and wherein the one or more images depict a surface of the photovoltaic cell.

18. The method as recited in claim 17, wherein the photovoltaic module is non-transparent.

19. The method as recited in claim 11, wherein the one or more images depict a surface of the encapsulant.

20. The method as recited in claim 11, comprising mapping chemical composition of the photovoltaic module across two dimensions based on the one or more images.

* * * * *